US011927582B2

(12) United States Patent
König

(10) Patent No.: US 11,927,582 B2
(45) Date of Patent: Mar. 12, 2024

(54) METHOD FOR TESTING A GAS SENSOR

(71) Applicant: TDK Corporation, Tokyo (JP)

(72) Inventor: Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 255 days.

(21) Appl. No.: 17/032,734

(22) Filed: Sep. 25, 2020

(65) Prior Publication Data

US 2021/0096115 A1   Apr. 1, 2021

(30) Foreign Application Priority Data

Sep. 26, 2019   (DE) .......................... 102019126024.8

(51) Int. Cl.
*G01N 33/00* (2006.01)
(52) U.S. Cl.
CPC ....... *G01N 33/007* (2013.01); *G01N 33/0016* (2013.01); *G01N 2033/0072* (2013.01)
(58) Field of Classification Search
CPC ............. G01N 33/0006; G01N 33/007; G01N 33/0016; G01N 2033/0072
See application file for complete search history.

(56) References Cited

U.S. PATENT DOCUMENTS

| | | | |
|---|---|---|---|
| 5,114,561 A * | 5/1992 | Bannister ........... | G01N 33/0016 204/424 |
| 10,746,712 B2 | 8/2020 | Martens et al. | |
| 2014/0331737 A1 * | 11/2014 | Kaneblei ........... | G01N 33/0006 73/1.06 |
| 2018/0335409 A1 | 11/2018 | Kao et al. | |
| 2019/0137465 A1 * | 5/2019 | Mizutani ........... | G01N 33/0016 |

FOREIGN PATENT DOCUMENTS

| | | | | |
|---|---|---|---|---|
| DE | 3717241 C1 * | 6/1988 | ......... | G01N 33/0006 |
| DE | 10150970 A1 | 4/2003 | | |
| DE | 102017004727 A1 | 11/2018 | | |
| EP | 1447664 A2 | 8/2004 | | |

OTHER PUBLICATIONS

Systems Plus Consulting, "Package Views & Dimensions," 2015, 2 pages.

* cited by examiner

*Primary Examiner* — Benjamin R Schmitt
(74) *Attorney, Agent, or Firm* — Slater Matsil, LLP

(57) ABSTRACT

A method for testing a gas sensor and a gas sensor are disclosed. In an embodiment a method for testing at least one gas sensor includes exposing in a first measurement the gas sensor to a test gas under first gas conditions including a first pressure and exposing in a second measurement the gas sensor to the test gas under second gas conditions including a second pressure, the second gas conditions being different from the first gas conditions, wherein the second pressure is different from the first pressure, and/or wherein the gas sensor is exposed to an intermediate pressure different from the first pressure between the first measurement and the second measurement.

18 Claims, 4 Drawing Sheets

METHOD FOR TESTING A GAS SENSOR

CROSS-REFERENCE TO RELATED APPLICATIONS

This application claims priority to German Patent Application No. 102019126024.8, filed on Sep. 26, 2019, which application is hereby incorporated herein by reference.

TECHNICAL FIELD

Embodiments of the present invention are related to a method for testing a gas sensor.

BACKGROUND

Gas sensors usually comprise a sensor device in a housing, which has an opening, also denoted as port, which allows the surrounding gas to enter the housing and to get into contact with the sensor device. State of the art gas sensors usually have large ports to provide the possibility for a quick gas exchange. However, sometimes it is necessary to use smaller gas ports, for instance due to technical reasons. For example, in connection with some pick-and-place devices a small port is necessary. Furthermore, in case a filter is needed, a smaller port allows the use of a smaller filter membrane. Consequently, a smaller port can lead to lower costs, since some filter materials can be very expensive, especially when a filter material is required that filters only certain gases. Moreover, a certain small port size can be required due to the customer environment. A smaller port can also reduce the risk of particle problems, since in case of a large port huge particles can enter the sensor easily and can cause malfunctions.

However, a small port can lead to the disadvantage that the sensor's response time to gas changes in the surrounding atmosphere is increased, since the gas molecules need more time to diffuse through the port. Even though the response time is not a big issue for many applications, because usually gas change rates are very slow as, for example, in connection with measurements of the air quality in a room, a small gas port leads to long testing times when the sensor undergoes testing and calibration, which is required before the sensor can be sold to a customer. During a usual testing procedure, the sensor is exposed to a gas and it is checked if the sensor responds in the desired way. Furthermore, calibration coefficients can be calculated based on the testing information. In usual testing methods the sensor to be tested is exposed first to clean air and then to a desired test gas, wherein the air or air/gas mixture is constantly lead to and from the testing chamber. The test gas is contained in pressurized bottles and is mixed with air using different flow rates to achieve desired concentrations. If the pressure in the chamber should remain constant, the total flow under normal conditions needs to be constant. Gas concentration changes therefore happen due to diffusion in the testing chamber. Even when using high flow rates, the gas exchange usually takes several tens of seconds even in an optimized chamber, which is a very long time for a high volume production. The gas exchange time can even increase for example when larger chambers with handlers and other required implements are used.

SUMMARY

Embodiments provide a method for testing a gas sensor, in particular a method that avoids or at least reduces some of the above-mentioned problems.

According to at least one embodiment, a method for testing at least one gas sensor comprises the step of exposing the gas sensor to a test gas. Here and in the following, the term "testing" preferably includes steps of basic functional testing the at least one gas sensor and/or of calibrating the at least one gas sensor in regard to at least one test gas species contained in the test gas.

Here and in the following, a gas sensor is a sensor that detects the presence of a gas, i.e., the presence of at least one gas species in a gas atmosphere in contact with the gas sensor. The gas sensor can preferably detect at least one gas species present in a mixture of gases. The gas atmosphere can be or comprise for instance air, i.e., clean air or normal air, which can be pure or which additionally contains a gas species as, for instance, CO, $CO_2$, ethanol and/or another environmental gas that is detected by the gas sensor.

When operated, the gas sensor provides an electrical signal, for example an electrical current and/or an electrical voltage and/or an electrical resistance and/or a digital signal and or a digital word, the electrical signal being a measure for the amount of the at least one detected gas species in the gas atmosphere. By measuring and processing the electrical signal of the gas sensor, preferably when operated under different predetermined gas conditions of the test gas, the testing can be carried out. Consequently, the method can preferably comprise several steps in which the at least one gas sensor is arranged in a test gas having different gas conditions. Here and in the following, the term "gas conditions" can include one or more features of a gas, which can be selected for instance from a gas composition, a gas pressure, a gas temperature. Particularly preferably, the change from one gas condition to another gas condition is at least partly carried out by means of a pressure change of the test gas as explained in further detail in the following.

The at least one gas sensor can for example comprise or be an electrochemical gas sensor, a pellistor-type gas sensor, a semiconductor gas sensor or a metal-oxide-semiconductor gas sensor. These types of gas sensors are well-known to a person skilled in the art and are therefore not further explained.

According to a further embodiment, the method is carried out in a testing chamber. Accordingly, the method can comprise the step of providing a testing chamber and arranging the at least one gas sensor in the testing chamber. The testing chamber preferably has an internal volume in which the at least one gas sensor is arranged and for which desired test gas conditions can be provided. Particularly preferably, a plurality of gas sensors can be arranged in the testing chamber, so that the method is carried out simultaneously for the plurality of gas sensors. The method steps and features described before and in the following equally apply to a method for testing exactly one gas sensor or for testing more than one gas sensor, i.e., a plurality of gas sensors, which are arranged at the same time in the test gas atmosphere.

According to a further embodiment, the method comprises a first measurement step, wherein in the first measurement step the at least one gas sensor is exposed to a test gas under first gas conditions including a first pressure. Preferably, a first electrical signal of the gas sensor is measured in the first measurement step. The electrical signal can preferably be a measure for the amount of a gas species that is part of the test gas of the first measurement step and that is detected by the gas sensor. The gas species that is detected by the gas sensor can be denoted here and in the following as test gas species.

According to a further embodiment, the method comprises a second measurement step, wherein in the second measurement step the gas sensor is exposed to a test gas under second gas conditions including a second pressure, the second gas conditions being different from the first gas conditions. Preferably, a second electrical signal of the gas sensor is measured in the second measurement step, the second electrical signal preferably being a measure for the test gas species in the test gas of the second measurement step.

Furthermore, it can be possible that at least one further measurement step is performed, during which the gas sensor is exposed to a test gas under further gas conditions including a further pressure, wherein the further gas conditions are different at least from the gas conditions of the measurement step immediately before. Preferably, a further electrical signal of the gas sensor is measured in the further measurement step. Furthermore, a plurality of such further measurement steps can be performed. Although in the following the method is mainly described having a first and a second measurement step, the description applies accordingly to a method comprising one or more further measurement steps. The measured electrical signals and the information of the accompanying gas conditions during the first, second and, if applicable, further measurement steps can be used for the basic functional testing and, in particular, for the calibration of the gas sensor.

According to a further embodiment, the testing chamber has an inlet and an outlet. The inlet is intended and embodied for filling the internal volume of the testing chamber with a test gas, whereas the outlet is intended and embodied for at least partly removing the test gas from the internal volume of the testing chamber. The outlet can be connected to a pump or an external volume with a pressure lower than the internal volume. The inlet can be connected to a gas source. If the inlet is closed and the outlet is open, so that the internal volume can be pumped, a decrease of the pressure can be achieved in the internal volume. The decrease of the pressure can lead to a vacuum. The term "vacuum" includes gas conditions with a pressure of equal to or less than 300 hPa, which can be denoted as rough vacuum, or equal to or less than 1 hPa, which can be denoted as fine vacuum, or equal to or less than $10^{-3}$ hPa, which can be denoted as high vacuum or even ultra-high vacuum depending on the pressure. If the inlet is open and the outlet is closed and the pressure in the internal volume is lower than the pressure of the gas source, gas can be filled into the internal volume. The gas exchange due to pressure differences can be very fast compared to gas exchanges due to diffusion processes.

During the first measurement step and the second measurement step at least one of the inlet and outlet is closed. Preferably, at least the outlet is closed during each of the first measurement step and the second measurement step. By closing the outlet or, preferably, both the inlet and the outlet of the testing chamber during the measurement steps, the test gas atmosphere, i.e., the gas conditions of the test gas, can be kept constant in the testing chamber. In other words, during each of the measurements step comprising the first measurement step and the second measurement step there is preferably no gas flow into, through and out of the testing chamber.

According to a further embodiment, the second pressure is different from the first pressure. Accordingly, the second pressure is lower than the first pressure or the second pressure is higher than the first pressure. Preferably, the pressure of the test gas is changed when changing from the first pressure to the second pressure. Particularly preferably, in this case in the first and second measurement step the test gas is substantially the same. "Substantially the same" means that the composition of the test gas, i.e., the relative concentration of the one or more gas species of the test gas, is not willingly changed from the first to the second measurement step and thus stays the same. Rather than changing a gas composition of the test gas, merely the gas pressure of the test gas can be changed by removing some of the test gas from the testing chamber or increasing the amount of the test gas in the testing chamber. Accordingly, the test gas comprises a test gas species with a relative concentration that is substantially the same during the first and second measurement step.

Due to the pressure change of the test gas between the first and second measurement step, the partial pressure of the test gas species detected by the gas sensor changes. Since a change of the partial pressure is equivalent to a concentration change of the detected test gas species, the gas sensor can react to the pressure change in a similar way as when a corresponding change of the gas composition is performed. If the gas sensor additionally exhibits a pressure dependency, this pressure dependency can for example be corrected for by developing a suitable model. For instance, the first and the second measurement step can be performed several times, wherein for each repetition of the first and second measurement step the amount of the detected test gas species in the test gas is changed, while each first measurement step is carried out with the same first pressure and each second measurement step is carried out with the same second pressure.

According to a further embodiment, the method comprises an intermediate step between the first measurement step and the second measurement step. During the intermediate step, the gas sensor is exposed to an intermediate pressure different from the first pressure. In particular, the intermediate pressure can be as low as possible. Preferably, the gas sensor is exposed to a vacuum during the intermediate step. This can mean that during the intermediate step the test gas of the first measurement step is substantially removed from the testing chamber. After the intermediate step, a test gas that is to be used during the second measurement step is fed into the testing chamber. In this case it can be possible that the test gas used during the first measurement step and the test gas used during the second measurement step are different. In particular, the concentration of the test gas species that is detected by the gas sensor is different in the test gases used during the first and the second measurement steps. Preferably, the first and the second pressure can be the same. Alternatively, the first and the second pressure can be different.

According to a further embodiment, the different gas conditions in the first and second measurement step can include different gas temperatures. In other words, alternatively or in addition to the variations of the first and second gas conditions described before, the test gas during the first measurement step can have a first temperature and the test gas during the second measurement step can have a second temperature which is different to the first temperature. It can be possible that the test gas during the first and second measurement step is unchanged so that the temperature difference causes a pressure difference. Alternatively, the by adapting the test gas pressure, the first and second pressure can be the same while the first and second temperatures are different. Furthermore, the first and second measurement steps can differ in regard to other physical stimuli for the gas sensor.

According to a further embodiment, the test gas comprises one or more of the following gas compounds: $N_2$, $O_2$, $CO_2$, CO, ethanol, $NH_3$, $N_xO_x$, volatile organic compounds (VOCs). In particular, the test gas can comprises one or more of the mentioned gas compounds in the first measurement step and in the second measurement step. Furthermore, the test gas can be a mixture with at least two or more of the mentioned gas compounds. For instance, the test gas can comprise or be a mixture of $N_2$, $O_2$ and at least one of $CO_2$, CO, ethanol, $NH_3$, $N_xO_x$, VOCs.

As described before, the method uses pressure changes to calibrate the at least one gas sensor. In particular, the method comprises pressure changes of the test gas after the first measurement step. While pressure changes take place with the speed of sound, which is about 333 m/s, diffusive gas changes, which are usually used in testing methods for gas sensors, take place with a typical speed of about 0.1 m/s to 1 m/s. Therefore, changes of the gas conditions between the first and second measurement step in the method described here happen much faster than in usual testing methods. The method described here therefore allows for a reduction of the required test time even in case the tested gas sensor or sensors has/have a small gas port. The described method, however, is not restricted to certain port sizes and can be carried out for gas sensors with any port size.

BRIEF DESCRIPTION OF THE DRAWINGS

Further features, advantages and expediencies will become apparent from the following description of exemplary embodiments in conjunction with the figures.

DETAILED DESCRIPTION OF ILLUSTRATIVE EMBODIMENTS

Equal or similar elements as well as elements of equal function are designated with the same reference signs in the figures. The figures and the proportions of the elements shown in the figures are not regarded as being shown to scale. Rather, single elements, in particular layers, can be shown exaggerated in magnitude for the sake of better presentation and/or better understanding.

Figure 1:
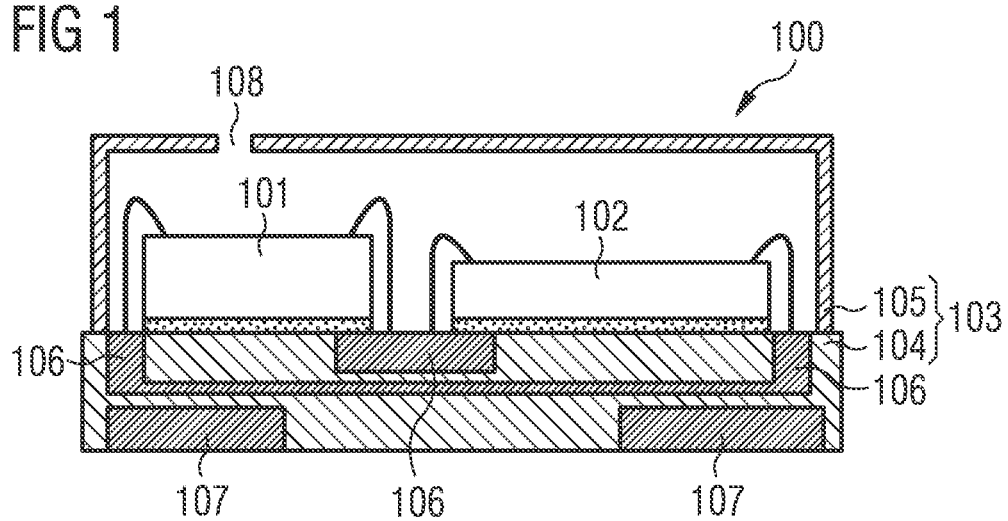
FIGS. 1-3 show schematic illustrations of gas sensors according to several embodiments.
Figure 2:
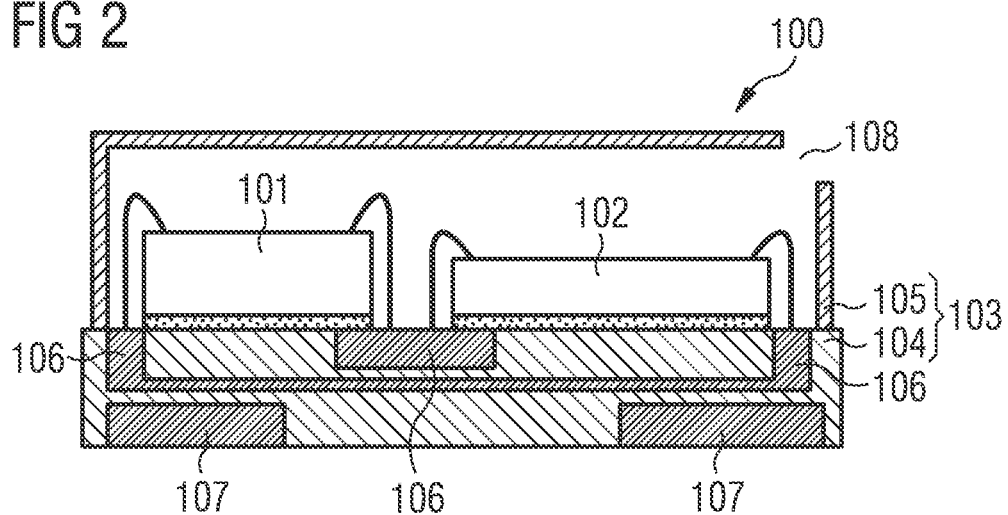
Figure 3:
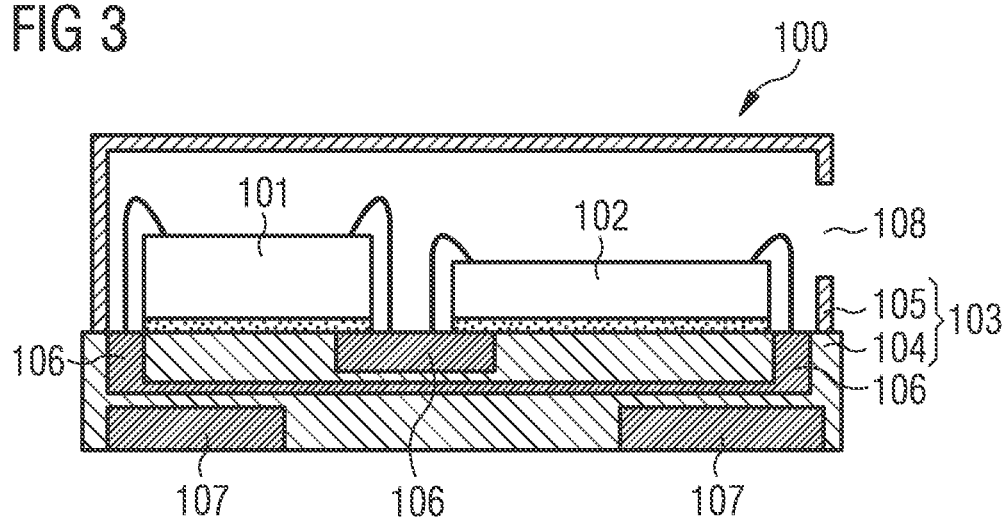

FIG. 1 shows a gas sensor 100 according to an embodiment. FIGS. 2 and 3 show modifications of the gas sensor 100 according to further embodiments. The features of the gas sensor 100 as illustrated in FIGS. 1 to 3 as well as in the following figures are purely exemplary and not to be understood as being delimiting the method explained below.

The gas sensor 100 comprises a sensor device 101, which is the gas-sensitive element of the gas sensor 100 and which can, for instance, be an electrochemical gas sensor, a pellistor-type gas sensor, a semiconductor gas sensor or a metal-oxide-semiconductor gas sensor. As indicated in FIG. 1, the sensor device 101 can be a chip or at least a chip-size device.

For example, the sensor device 101 is or comprises a MEMS device (MEMS: microelectromechanical system). Furthermore, the gas sensor 100 can comprise an electronic device 102, which, for example, is or comprises an ASIC (application-specific integrated circuit). Such device can for example control the function of the sensor device 101 and, thus, of the gas sensor 100. The electronic device 102 can be mounted together with the sensor device 101 in a common housing 103 or outside of the housing 103. Alternatively, it can be possible that the gas sensor 100 does not comprise an electronic device 102.

The housing 103 comprises a carrier 104 carrying the sensor device 101 and the electronic device 102, which, for example, can be soldered or glued to the carrier 104 by means of a solder layer or glue layer and electrically contacted via bond wires. Furthermore, the housing 103 comprises a cover 105 covering the sensor device 101 and the electronic device 102. Both the carrier 104 and the cover 105 can comprise a ceramic and/or plastics material. Alternatively, the cover 105 can for example also comprise or consist of a metal. For electrically contacting the devices mounted on the carrier 104, the carrier 104 further comprises internal electrical contacts as, for instance, bond pads 106, external electrical contacts as, for instance, solder pads 107 and, if necessary, internal conduction lines and/or electrical vias. The cover 105 comprises an opening which forms a port 108, through which the surrounding atmosphere can enter the housing 103, so that the gas or one or more gas species of the surrounding atmosphere can be detected by the sensor device 101.

As shown in FIG. 1, the port 108 can be in the top side of the cover 105 so that the surrounding gas atmosphere can enter the housing 103 from the top of the gas sensor 100. Consequently, the gas sensor 100 is to be mounted with the carrier 104 on a support so that the port 108 is accessible. FIG. 2 shows a further embodiment of a gas sensor 100 having a port 108 in the top side and a lateral side of the cover 105. FIG. 3 shows a further embodiment of a gas sensor 100 having a port 108 only in the lateral side of the cover 105. In these two embodiments the gas of the surrounding atmosphere can enter the housing 103 even if the gas sensor 100 is mounted upside-down with the cover 105 on a support.

Figure 4:
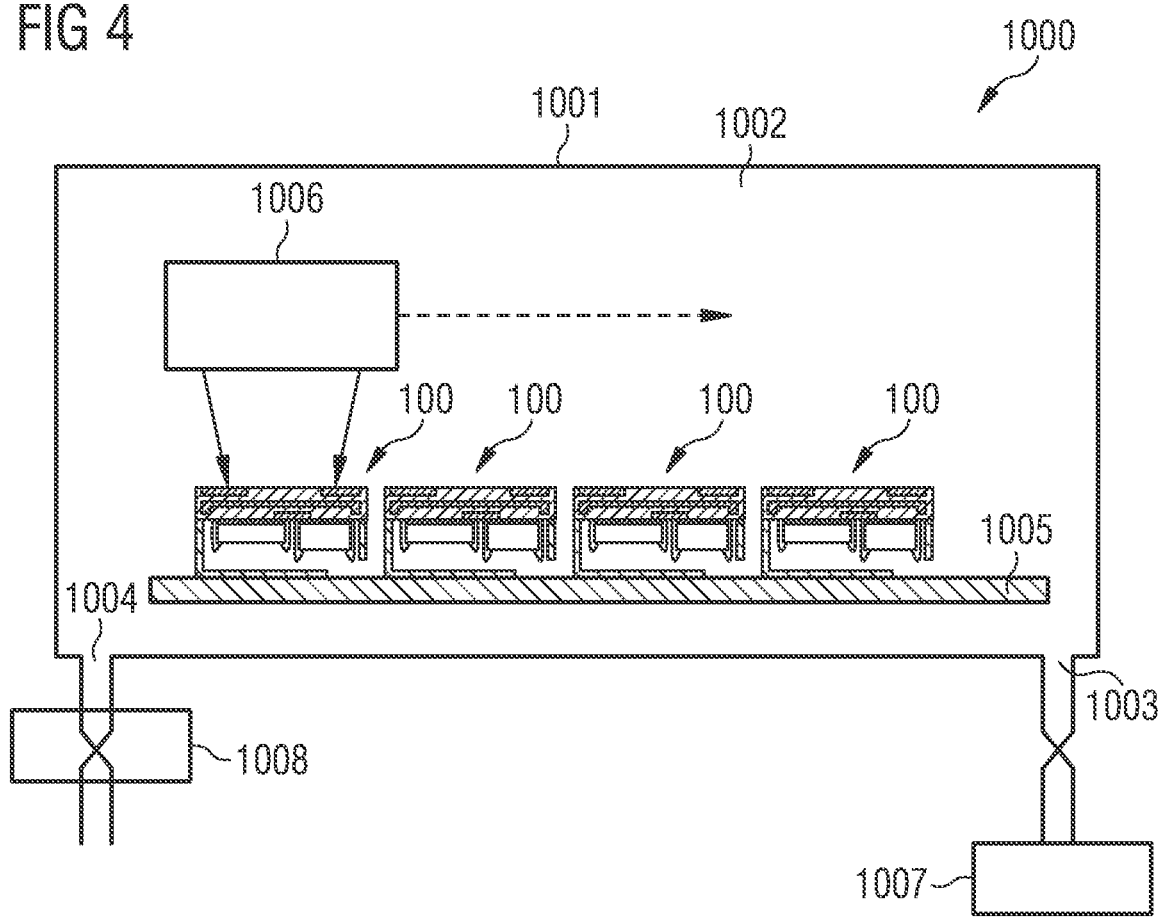
FIG. 4 shows a schematic illustration of a measurement device according to a further embodiment.

FIG. 4 shows a measurement device 1000 which is embodied for carrying out a method for testing at least one gas sensor 100. The measurement device 1000 comprises a testing chamber 1001, in which the method is carried out. The testing chamber 1001 encloses an internal volume 1002 in which the at least one gas sensor 100 is arranged and for which desired test gas conditions can be provided. In the embodiment shown a plurality of gas sensors 100 is arranged in the testing chamber 1001, so that the method can be carried out for the plurality of gas sensors 100.

The testing chamber 1001 has an inlet 1003 and an outlet 1004. The inlet 1003 is embodied for filling the internal volume 1002 of the testing chamber 1001 with a test gas, whereas the outlet 1004 is embodied for at least partly removing the test gas from the internal volume 1002 of the testing chamber 1001. The gas sensors 100 are arranged in a matrix-like order on a support 1005, which can comprise or be, for example, a mounting tape, and can be contacted by a testing device 1006. In order to facilitate the contacting via the testing device 1006, which needs to access the electrical contacts of the gas sensors 100, the gas sensors 100 are arranged upside-down on the support 1005. The gas sensors 100 are embodied as explained in connection with FIG. 2, having a port at least partly on a lateral side of the cover, so that the ports of the gas sensors 100 are not blocked by the support 1005. Alternatively, the gas sensors 101 can also be embodied as shown in FIG. 3. However, the method can be carried out also in connection with other gas sensors and other arrangements of gas sensors. The testing device 1006 electrically contacts one gas sensor 100 after the other as indicated by the arrows by stepping from gas sensor 100 to gas sensor 100, thereby measuring an electrical signal of the gas sensors 100 in response to the test gas contained in the testing chamber 1001. Alternatively, the measurement device 1000 can have a testing device that contacts more than one gas sensor 100 or even all gas sensors 100 at the same time.

The inlet 1003 is connected to a gas source 1007, which can comprise one or more pressurized bottles containing gases or gas species. The outlet 1004 can be connected to a pump or an external volume with a pressure lower than the internal volume 1001. In the embodiment shown in FIG. 4, a pressure controller 1008 is connected to the outlet 1004, so that the pressure of the test gas in the internal volume 1002 of the testing chamber 1001 can be controlled. When the inlet 1003 is closed and the outlet 1004 is open, a controlled decrease of the pressure in the internal volume 1002 can be achieved by means of the pressure controller 1008. If the inlet 1003 is open and the outlet 1004 is closed, gas can be filled into the internal volume 1002.

The test gas can preferably comprise one or more of the following gas compounds: $N_2$, $O_2$, $CO_2$, CO, ethanol, $NH_3$, $N_xO_x$, volatile organic compounds (VOCs). For instance, the test gas can comprise or be a mixture of $N_2$, $O_2$ and at least one of $CO_2$, CO, ethanol, $NH_3$, $N_xO_x$, VOCs.

Figure 5:
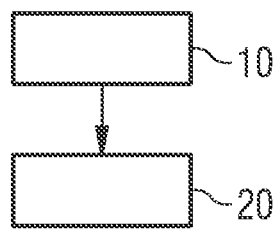
FIG. 5 shows a schematic illustration of method steps of a method for testing a gas sensor according to a further embodiment.

FIG. 5 shows method steps of a method for testing at least one gas sensor, wherein the method steps can be carried out with the measurement device 1000 of the embodiment shown in FIG. 4.

The method comprises a first measurement step 10. In the first measurement step 10 the at least one gas sensor is exposed to a test gas under first gas conditions including a first pressure. A first electrical signal of the at least one gas sensor is measured in the first measurement step. As explained in connection with FIG. 4, the testing device 1006 is used to measure the electrical signal of the gas sensors 100 arranged in the testing chamber 1001. In particular, in the first measurement step 10 an electrical signal of every gas sensor is measured, wherein the electrical signals depend on the first gas conditions. The electrical signal of each gas sensor is a measure for the amount of a test gas species that is part of the test gas present in the internal volume of the testing chamber during the first measurement step 10 and that is detected by the respective gas sensor.

The method further comprises a second measurement step 20, wherein in the second measurement step the at least one gas sensor, i.e., the plurality of gas sensors in the embodiment of FIG. 4, is exposed to a test gas under second gas conditions including a second pressure. The second gas conditions are different from the first gas conditions. Similarly to the first measurement step 10, a second electrical signal of each of the gas sensors is measured in the second measurement step, the second electrical signal preferably being a measure for the test gas species in the test gas of the second measurement step 20.

During the first measurement step 10 and the second measurement step 20 at least one of the inlet and outlet of the testing chamber is closed. Preferably, at least the outlet is closed during each of the first measurement step 10 and the second measurement step 20. By closing the outlet or, preferably, both the inlet and the outlet of the testing chamber, the test gas atmosphere, i.e., the gas conditions of the test gas, can be kept constant in the testing chamber. Consequently, during the each of the first measurement step 10 and the second measurement step 20 there is no gas flow into, through and out of the testing chamber.

The second pressure is different from the first pressure. In particular, in the shown embodiment the second pressure is lower than the first pressure. However, it can also be possible that the second pressure is higher than the first pressure. Particularly preferably, in the first and second measurement step 10, 20 the test gas is substantially the same. Consequently, the first and second gas conditions differ only in regard to the gas pressure. Due to the pressure change of the test gas between the first and second measurement step 10, 20 the partial pressure of the test gas species that is detected by the gas sensors changes. The partial pressure change is equivalent to a concentration change of the test gas species.

For example, if an oxygen sensor, which can be a gas sensor comprising a sensor device formed by a metal oxide gas sensor, should be tested and, in particular, calibrated, the testing chamber can be filled with clean air at a pressure of 1000 hPa as test gas for the first measurement step 10. The partial pressure of oxygen is about 200 hPa. The gas sensor can therefore be tested with a concentration of $(200/1000) *(1/22.4)$ mol/l=4.48 mol/l. For the second measurement step 20, the pressure in the testing chamber is reduced for example to 500 hPa, resulting in an oxygen concentration of 2.24 mol/l. The gas sensor can then be tested also at this concentration and consequently be calibrated. Due to the fact that gas changes in a gas, which is kept at the same pressure, are purely diffusive and take place with a speed of about 0.1 m/s to 1 m/s, whereas changes of pressure take place with the speed of sound, i.e., with a speed of about 333 m/s, the method described herein is much faster than usual gas sensor calibration methods. If the gas sensor additionally exhibits a pressure dependency, this pressure dependency can for example be corrected for by developing a suitable model.

Figure 6:
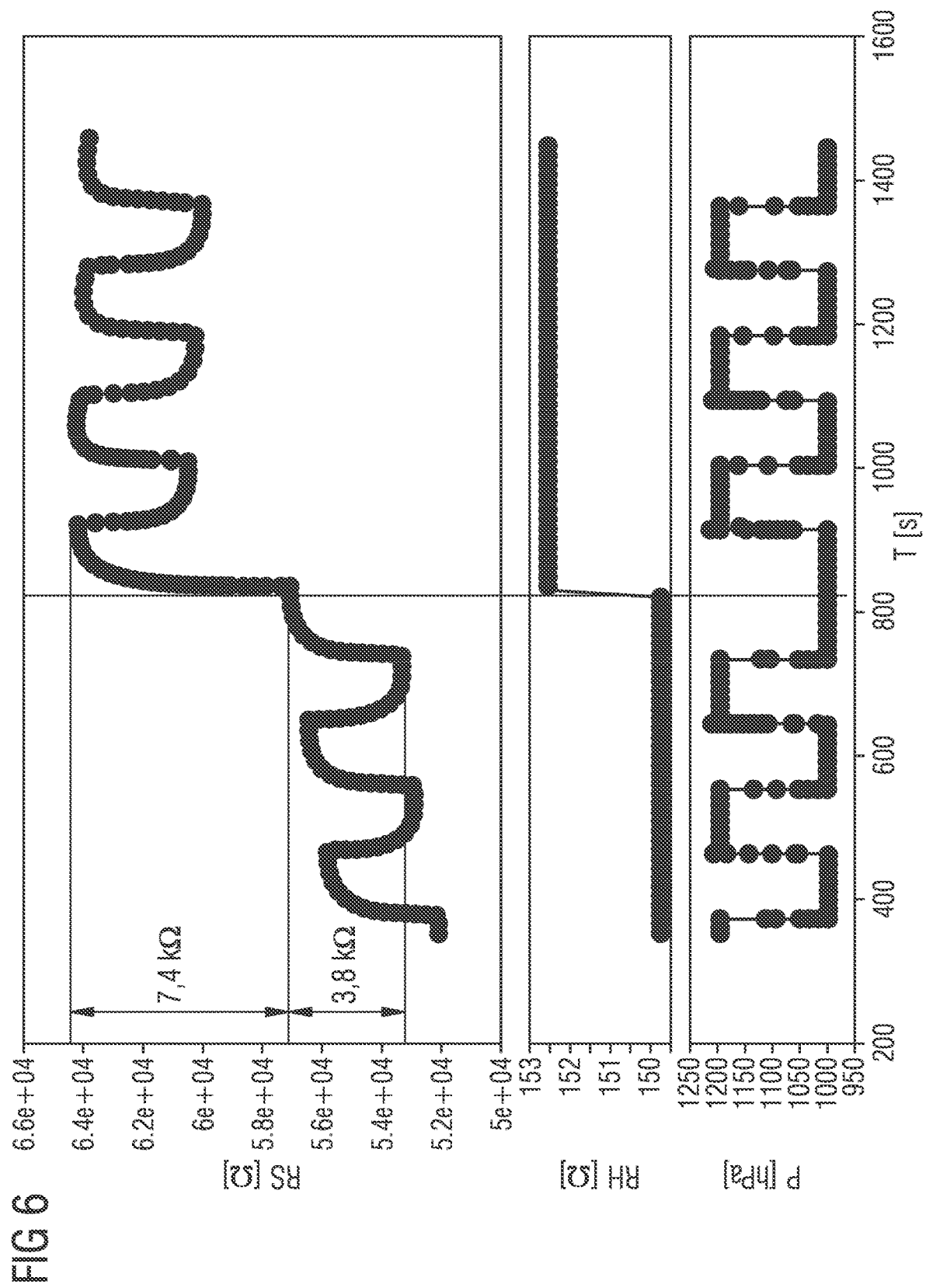
FIG. 6 shows a measurement of a gas sensor.

FIG. 6 shows an exemplary measurement with a gas sensor in a measurement device as explained above. The topmost measurement shows as sensor reading, i.e., as the electrical signal of the gas sensor, the electrical resistance RS of the gas sensor in response to pressure changes of the pressure P (lowermost measurement) and the temperature T, measured in terms of a heater resistance RH (middle measurement), in a testing chamber, while performing a succession of first and second measurement steps during a time T. As can be easily seen, the pressure changes of about 200 hPa cause significant changes of the sensor reading of about 3.8 kΩ. Although the temperature change in the testing chamber at a time T=810 s causes a shift of the sensor reading, the sensor reading difference between the first and second measurement steps stay the same.

Figure 7:
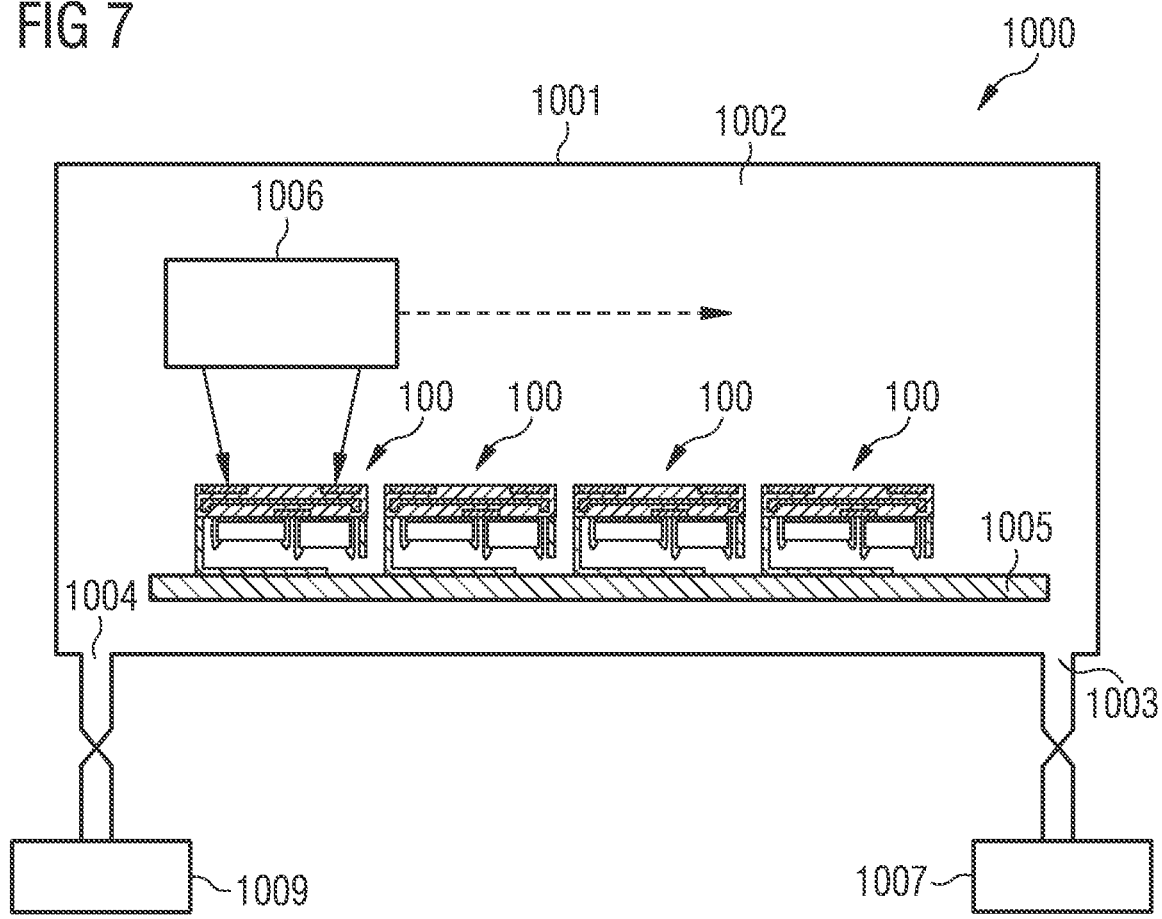
FIG. 7 shows a schematic illustration of a measurement device according to a further embodiment.
Figure 8:
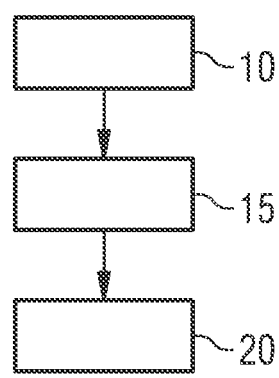
FIG. 8 shows a schematic illustration of method steps of a method for testing a gas sensor according to a further embodiment.

FIG. 7 shows a measurement device 1000 which is embodied for carrying out a method for testing at least one gas sensor 100 according to a further embodiment, wherein the method is shown in FIG. 8. The method, which is a modification of the method shown in FIG. 5, comprises an intermediate step 15 between the first and second measurement step 10, 20. During the intermediate step 15 the gas sensors 100 are exposed to an intermediate pressure different from the first pressure. Preferably, the gas sensors 100 are exposed to a vacuum during the intermediate step 15. Consequently, the test gas contained in the testing chamber 1001 during the first measurement step 10 is substantially removed from the testing chamber 1001 in the intermediate step 15. For this purpose, the measurement device 1000 comprises a vacuum-generating device 1009, for instance a pump or a large vacuum reservoir, connected to the outlet 1004.

After the intermediate step 15, a test gas, which is then used during the second measurement step 20, is fed into the testing chamber 1001 via the inlet 1003. In particular, the test gas used during the first measurement step 10 and the test gas used during the second measurement 20 step are different. For instance, the test gas used during the first measurement step 10 is clean air and the test gas used during the second measurement step 20 is clean air mixed with a test gas species, which can be, for instance, CO, $CO_2$, ethanol and/or other environmental gases. In general, the concentration of the test gas species that is detected by the gas sensor is different in the test gases used during the first and the second measurement steps 10, 20. Preferably, the first and the second pressure can be the same. Alternatively, the first and the second pressure can be different. Since the gas sensor is exposed to vacuum during the intermediate step 15, the exchange of test gases is much faster than in a method, in which changes of the concentration of the test gas species only take place by diffusion.

In the methods explained above, a repetition of first and second measurements can be performed as also mentioned in connection with FIG. 6. Additionally or alternatively, one or more further measurement steps can be performed, wherein in each of the further measurement steps the gas sensor(s) is/are exposed to a test gas under further gas conditions including a further pressure, wherein the further gas conditions are different at least from the gas conditions of the measurement step immediately before.

Alternatively or additionally to the features described in connection with the figures, the embodiments shown in the figures can comprise further features described in the general part of the description. Moreover, features and embodiments of the figures can be combined with each other, even if such combination is not explicitly described.

The invention is not restricted by the description on the basis of the exemplary embodiments. Rather, the invention encompasses any new feature and also any combination of features, which in particular comprises any combination of features in the patent claims, even if this feature or this combination itself is not explicitly specified in the patent claims or exemplary embodiments.

What is claimed is:

1. A method comprising:
    exposing in a first measurement a gas sensor to a test gas under first gas conditions including a first pressure;
    exposing in a second measurement the gas sensor to the test gas under second gas conditions including a second pressure, the second gas conditions being different from the first gas conditions,
    wherein the second pressure is different from the first pressure,
    wherein the gas sensor is exposed to an intermediate pressure different from the first pressure between the first measurement and the second measurement, and
    wherein the method is a method for testing the gas sensor;
    performing the method in a testing chamber; and
    during a time between the first and second measurements, removing the test gas of the first measurement from the testing chamber,
    wherein the gas sensor is exposed to a vacuum during the time between the first and second measurements.

2. The method according to claim 1, wherein the second pressure is lower than the first pressure.

3. The method according to claim 1, wherein the second pressure is higher than the first pressure.

4. The method according to claim 1, further comprising changing a pressure of the test gas between the first and second measurements from the first pressure to the second pressure.

5. The method according to claim 1, wherein during the first and second measurements the test gas is substantially the same.

6. The method according to claim 1, wherein the test gas comprises a test gas species with a relative concentration that is substantially the same during the first and second measurements.

7. The method according to claim 1, wherein the test gas during the first and the second measurements is different.

8. The method according to claim 1, further comprising:
    performing the method in the testing chamber having an inlet and an outlet, wherein during the first measurement and the second measurement at least the outlet is closed.

9. The method according to claim 1, further comprising:
    performing the method simultaneously for a plurality of gas sensors in the testing chamber.

10. The method according to claim 1, wherein the test gas comprises a mixture of N2, O2 and at least one of CO2, CO, ethanol, NH3, NxOx, or volatile organic compounds.

11. The method according to claim 1, wherein the test gas comprises a mixture of N2, O2 and CO.

12. The method according to claim 1, wherein the test gas comprises a mixture of N2, O2 and NH3.

13. The method according to claim 1, wherein the test gas comprises a mixture of N2, O2 and ethanol.

14. The method according to claim 1, wherein the test gas comprises a mixture of N2, O2 and NxOx.

15. A method comprising:
    exposing a gas sensor in a first measurement in a testing chamber to a test gas under first gas conditions including a first pressure of the test gas;
    exposing the gas sensor, in a second measurement in the testing chamber, to the test gas under second gas conditions including a second pressure of the test gas, the second gas conditions being different from the first gas conditions,
    wherein the second pressure is different from the first pressure,
    wherein the gas sensor is exposed to an intermediate pressure different from the first pressure between the first measurement and the second measurement, and
    wherein the method is a method for testing the gas sensor arranged in an internal volume of the testing chamber; and
    Performing the method in the testing chamber having an inlet and an outlet,
    wherein during the first measurement and the second measurement at least the outlet is closed.

16. The method according to claim 15, wherein the test gas comprises a mixture of N2, O2 and at least one of CO or ethanol.

17. The method according to claim 15, wherein the test gas comprises a mixture of N2, O2 and at least one of NH3 or NxOx.

18. A measurement device comprising:
    a testing chamber comprising a gas inlet and a gas outlet and an internal volume for arranging at least one gas sensor,
    wherein the measurement device is configured to:

perform a first measurement in which the at least one gas sensor is exposed in the testing chamber to a test gas under first gas conditions including a first pressure of the test gas;

perform a second measurement in which the at least one gas sensor is exposed in the testing chamber to the test gas under second gas conditions including a second pressure of the test gas, the second gas conditions being different from the first gas conditions, wherein the second pressure is different from the first pressure, and wherein the gas sensor is exposed to an intermediate pressure different from the first pressure between the first measurement and the second measurement; and perform the first and second measurements in the testing chamber; and during a time between the first and second measurements, remove the test gas of the first measurement from the testing chamber, wherein the gas sensor is exposed to a vacuum during the time between the first and second measurements; or performing the first and second measurements in the testing chamber, wherein during the first measurement and the second measurement at least the outlet is closed.

\* \* \* \* \*